US010278619B2

(12) United States Patent
Wulf et al.

(10) Patent No.: US 10,278,619 B2
(45) Date of Patent: May 7, 2019

(54) METHOD AND DEVICE FOR DISTINGUISHING BLINKING EVENTS AND INSTRUMENT GAZES USING AN EYE OPENING WIDTH

(71) Applicant: Robert Bosch GmbH, Stuttgart (DE)

(72) Inventors: Felix Wulf, Ludwigsburg (DE); Tjark Vandommele, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/574,364

(22) PCT Filed: Apr. 26, 2016

(86) PCT No.: PCT/EP2016/059233
§ 371 (c)(1),
(2) Date: Nov. 15, 2017

(87) PCT Pub. No.: WO2016/206831
PCT Pub. Date: Dec. 29, 2016

(65) Prior Publication Data
US 2018/0132759 A1    May 17, 2018

(30) Foreign Application Priority Data

Jun. 22, 2015   (DE) .................. 10 2015 211 444

(51) Int. Cl.
*A61B 5/11*   (2006.01)
*A61B 3/113*   (2006.01)
(Continued)

(52) U.S. Cl.
CPC ............ *A61B 5/1103* (2013.01); *A61B 3/102* (2013.01); *A61B 3/113* (2013.01); *A61B 3/145* (2013.01);
(Continued)

(58) Field of Classification Search
None
See application file for complete search history.

(56) References Cited

U.S. PATENT DOCUMENTS 4,144,531 A * 3/1979 Anbergen ............ A61B 5/1103
340/575
4,359,724 A * 11/1982 Zimmerman .......... G08B 21/06
340/575
(Continued)

FOREIGN PATENT DOCUMENTS

EP    2351524 A1   8/2011
JP    2002029279 A  1/2002
(Continued)

OTHER PUBLICATIONS

International Search Report dated Jun. 24, 2016, of the corresponding International Application PCT/EP2016/059233 filed Apr. 25, 2016.

*Primary Examiner* — Curtis J King
(74) *Attorney, Agent, or Firm* — Norton Rose Fulbright US LLP; Gerard Messina

(57) ABSTRACT

A method for distinguishing blinking events and instrument gazes on the basis of an eye-opening width. The eye-opening width represents an instantaneously detected clearance between the eyelids of an eye. In a step of ascertaining, a blinking event is ascertained using at least one blinking limit value. The blinking event is ascertained when an opening width value, which represents the eye-opening width, is smaller than the blinking limit value. In a step of determining, an instrument gaze is determined using a maximum blinking duration. The instrument gaze is determined when the detected blinking event is detected as lasting longer than the maximum blinking duration. The steps of the method are (Continued)

able to be carried out anew when the opening width value is greater than an open limit value following the determination of the instrument gaze.

17 Claims, 3 Drawing Sheets

(51) Int. Cl.
| | |
|---|---|
| *A61B 5/18* | (2006.01) |
| *A61B 5/00* | (2006.01) |
| *G08B 21/06* | (2006.01) |
| *A61B 3/10* | (2006.01) |
| *A61B 3/14* | (2006.01) |
| *G06K 9/00* | (2006.01) |

(52) U.S. Cl.
CPC ............. *A61B 5/1128* (2013.01); *A61B 5/18* (2013.01); *A61B 5/4809* (2013.01); *A61B 5/7282* (2013.01); *G06K 9/0061* (2013.01); *G06K 9/00845* (2013.01); *G08B 21/06* (2013.01)

(56) References Cited

U.S. PATENT DOCUMENTS

| | | | | |
|---|---|---|---|---|
| 4,725,824 A * | 2/1988 | Yoshioka | ............... | G08B 21/06 340/575 |
| 4,953,111 A * | 8/1990 | Yamamoto | ........... | A61B 5/1103 340/575 |
| 5,239,337 A * | 8/1993 | Takagi | .................. | G03B 7/091 396/242 |
| 5,311,877 A * | 5/1994 | Kishi | ..................... | G08B 21/06 340/575 |
| 5,570,698 A * | 11/1996 | Liang | ..................... | A61B 3/113 340/575 |
| 5,689,241 A * | 11/1997 | Clarke, Sr. | ............... | A61B 5/18 340/575 |
| 5,786,765 A * | 7/1998 | Kumakura | ............. | G08B 21/06 340/575 |
| 5,795,306 A * | 8/1998 | Shimotani | ............ | A61B 5/1103 600/558 |
| 6,304,187 B1 * | 10/2001 | Pirim | ........................ | B60R 1/04 340/573.1 |
| 6,661,345 B1 * | 12/2003 | Bevan | ..................... | G08B 21/06 340/575 |
| 7,301,464 B2 * | 11/2007 | Coulter | ............... | B60K 28/066 340/573.1 |
| 7,301,465 B2 * | 11/2007 | Tengshe | ................. | G08B 21/06 340/575 |
| 7,344,251 B2 * | 3/2008 | Marshall | ................ | A61B 3/112 351/210 |
| 7,438,418 B2 * | 10/2008 | Marshall | .................. | A61B 5/16 351/210 |
| 8,340,368 B2 * | 12/2012 | Lee | ........................... | C23C 8/80 280/730.1 |
| 9,888,874 B2 * | 2/2018 | Nakajima | ............ | A61B 5/0075 |
| 2002/0113943 A1 * | 8/2002 | Trajkovic | ............... | G02B 7/102 351/209 |
| 2004/0070509 A1 * | 4/2004 | Grace | .................. | A61B 5/1103 340/575 |
| 2004/0090334 A1 * | 5/2004 | Zhang | .................. | B60K 28/066 340/575 |
| 2004/0150514 A1 * | 8/2004 | Newman | ................ | B60Q 9/008 340/435 |
| 2004/0181168 A1 * | 9/2004 | Plant | ...................... | A61B 3/113 600/558 |
| 2004/0239509 A1 * | 12/2004 | Kisacanin | ................ | A61B 5/18 340/575 |
| 2005/0030184 A1 * | 2/2005 | Victor | .................... | B60K 28/06 340/576 |
| 2005/0159893 A1 * | 7/2005 | Isaji | ......................... | G01S 17/023 701/301 |
| 2006/0011399 A1 * | 1/2006 | Brockway | ................ | A61B 5/18 180/272 |
| 2006/0031005 A1 * | 2/2006 | Sakano | .............. | G01C 21/3638 701/455 |
| 2006/0083409 A1 * | 4/2006 | Yuzawa | ................. | G06Q 10/10 382/116 |
| 2006/0103539 A1 * | 5/2006 | Isaji | .......................... | B60J 3/04 340/575 |
| 2008/0150734 A1 * | 6/2008 | Johns | ....................... | A61B 5/18 340/575 |
| 2009/0109400 A1 * | 4/2009 | Yoshinaga | ............. | A61B 3/113 351/210 |
| 2012/0300061 A1 * | 11/2012 | Osman | .................. | G06F 1/3231 348/135 |
| 2012/0306637 A1 * | 12/2012 | McGough | ............. | B60K 37/06 340/439 |
| 2014/0093140 A1 * | 4/2014 | Juveneton | .......... | G06K 9/00906 382/117 |
| 2014/0225725 A1 * | 8/2014 | Takahashi | .............. | B60K 28/02 340/439 |
| 2015/0103312 A1 * | 4/2015 | Paille | ..................... | G02C 7/025 351/204 |
| 2015/0258997 A1 * | 9/2015 | Nilsson | ................. | B60W 40/09 340/576 |
| 2016/0302662 A1 * | 10/2016 | Suzuki | ..................... | G01B 11/25 |
| 2018/0017858 A1 * | 1/2018 | Dominguez-Montes | ..................... | G03B 35/24 |

FOREIGN PATENT DOCUMENTS

| | | |
|---|---|---|
| JP | 2003000571 A | 1/2003 |
| JP | 2008197821 A | 8/2008 |
| WO | 2014031042 A1 | 2/2014 |

\* cited by examiner

METHOD AND DEVICE FOR DISTINGUISHING BLINKING EVENTS AND INSTRUMENT GAZES USING AN EYE OPENING WIDTH

BACKGROUND INFORMATION

Drowsiness and microsleep events while driving frequently lead to dangerous situations or accidents.

The drowsiness of a driver of a vehicle is able to be indirectly estimated from his driving behavior.

Correlations between the characteristics of blinking events and drowsiness are discussed in the literature.

PCT Application No. WO 2014 031042 A1 describes fitting of an eye-opening signal with predefined modeled signals in order to detect blinking events and to draw conclusions therefrom as to the alertness of the driver.

SUMMARY

In accordance with the present invention, a method is provided for distinguishing between blinking events and gazes at instruments using an eye-opening width; the present invention also provides a device that utilizes this method, as well as a corresponding computer program. Advantageous refinements and improvements of the device are described herein.

Obtaining information about the drowsiness or sleepiness of a person with the aid of blinking events requires that only actual blinking events of the person be evaluated. However, eye movements voluntarily performed by the person that lead to reflex-type eyelid movements, such as lowering the direction of the gaze toward instruments of an instrument panel, for example, have initial characteristics of the lid movement that are similar to those of blinking events.

In accordance with the present invention, a distinction is therefore made between a blinking event and a lowered gaze, using a duration of the event as the basis since a blinking event should be concluded after a brief period of time.

A method is provided for distinguishing blinking events and gazes at instruments with the aid of an eye-opening width, the eye-opening width representing a currently detected clearance between the eyelids of an eye. The method has the following steps:

Ascertaining a blinking event using at least one blinking limit value, the blinking event being ascertained when an opening width value that represents a value of the eye-opening width is smaller than the blinking limit value; and Determining an instrument gaze using a maximum blinking duration, the instrument gaze being determined when the detected blinking event is detected as lasting longer than the maximum blinking duration, the steps of the method in particular being carried out anew when the opening width value is greater than an open limit value following the determination of the instrument gaze.

A blinking event may be understood as a blink, which starts with an open eye, followed by a closure of the eye for the most part, until the eye is opened once again. An instrument gaze may be understood as a gaze lowered to a speedometer display and/or to some other display of a vehicle. In particular, the instrument gaze may denote a gaze at a freely programmable instrument cluster. An eye-opening width may also be understood as an eye closure width. A lowered gaze that is shorter than the maximum blinking duration is evaluated as a blinking event.

In the step of ascertaining, a medium blinking event may be ascertained when the opening width value is lower than a medium blinking limit value. Furthermore, a deep blinking event may be ascertained when the opening width value is lower than a deep blinking limit value. In the same way, a deep blinking event may be ascertained when an opening width value following the ascertainment of the medium blinking event is lower than the deep blinking limit value. In this context, a medium blinking event is to be understood as a blinking event that features a medium eye-opening width, while a deep blinking event is understood as a blinking event that has a low eye-opening width, i.e. an eye-opening width that is smaller than the medium eye-opening width, or that is understood as a closed eye. An analysis of the instantaneous drowsiness of a person is able to be improved by distinguishing between medium blinking events and deep blinking events.

The instrument gaze may be determined when the medium blinking event is determined as lasting longer than the maximum blinking duration. As an alternative or in addition, no instrument gaze is able to be determined when the deep blinking event is ascertained as lasting longer than the maximum blinking duration. Separating medium blinking events and deep blinking events makes it easier to distinguish the instrument gazes.

The method may include a step of storing, in which a time characteristic of the opening width value is stored as a blinking event characteristic when the opening width value is greater than the blinking limit value following the ascertaining of the blinking event. After the step of storing, the steps of the method are able to be carried out anew. In the step of storing, opening width values within a certain time period may be stored, and the storing is able to take place retroactively. The starting instant of the time period to be stored may precede an onset of the blinking event. Storing of the blinking event characteristic allows for the further evaluation of the blinking event.

The method may include a step of interpolating, in which the opening width values of the blinking event characteristic are connected to form a curve. A curve allows for an uninterrupted evaluation of the blinking event.

The curve is able to be improved or approximated with the aid of a predefined curve shape. A calculation of the curve may be simplified using an expected curve shape. For example, the curve shape may reproduce a standardized blinking event, which is able to be adapted to the actual blinking event with the aid of one or a plurality of blinking parameter(s).

In the step of interpolating, at least one deviation value of at least one of the opening width values from the curve is able to be determined. A deviation value may represent a difference between a value of a curve point that corresponds to an opening width value and the opening width value. The curve may be optimized in a step-by-step manner. In the process, the error is able to be minimized by averaging across at least a majority of the stored opening width values.

The present method may include a step of plausibilizing, in which the blinking event characteristic is discarded if the at least one deviation value or a value derived therefrom, such as an average value, is greater than a deviation limit value.

Eliminating unusual blinking events makes it possible to determine the drowsiness of the person with an excellent degree of probability.

The present method may include a step of modifying, in which the blinking limit value and, alternatively or additionally, the open limit value, is/are adapted using a reference level for the eye-opening width. The reference level represents the eye-opening width when no blinking event is present and an instrument gaze is occurring alternatively or additionally. In the same way, the medium blinking limit value and/or the deep blinking limit value is/are able to be adapted using the reference level. As a result, the method proposed here functions regardless of factors that affect the eye-opening width outside of blinking events and/or instrument gazes.

For example, this method may be implemented in the form of software or hardware or in a mixed form of software and hardware, for instance in a control unit.

In addition, the approach introduced here provides a device which is designed to carry out, actuate and/or implement the steps of a variant of a method presented here in corresponding devices. This specific embodiment variant of the present invention in the form of a device may also be used for rapidly and efficiently achieving the objective on which the present invention is based.

In this context, a device may be understood as an electrical device that processes sensor signals and outputs control and/or data signals as a function of such processing. The device can include an interface, which may be developed in the form of hardware and/or software. In the case of a hardware development, the interfaces may be part of what is commonly known as a system ASIC, for example, which includes a wide variety of functions of the device. However, it is also possible that the interfaces are separate, integrated switching circuits or are at least partially made up of discrete components. In the case of a software design, the interfaces may be software modules that are provided on a microcontroller in addition to other software modules.

Also advantageous is a computer program product or a computer program having program code, which is able to be stored on a machine-readable carrier or a storage medium such as a semiconductor memory, a hard disk memory, or an optical memory and which is used for executing, implementing and/or actuating the steps of the present method according to one of the afore-described specific embodiments, in particular when the program product or the program is running on a computer or on a device.

Exemplary embodiments of the present invention are illustrated in the figures and described in greater detail below.

DETAILED DESCRIPTION OF EXAMPLE EMBODIMENTS

Figure 1:
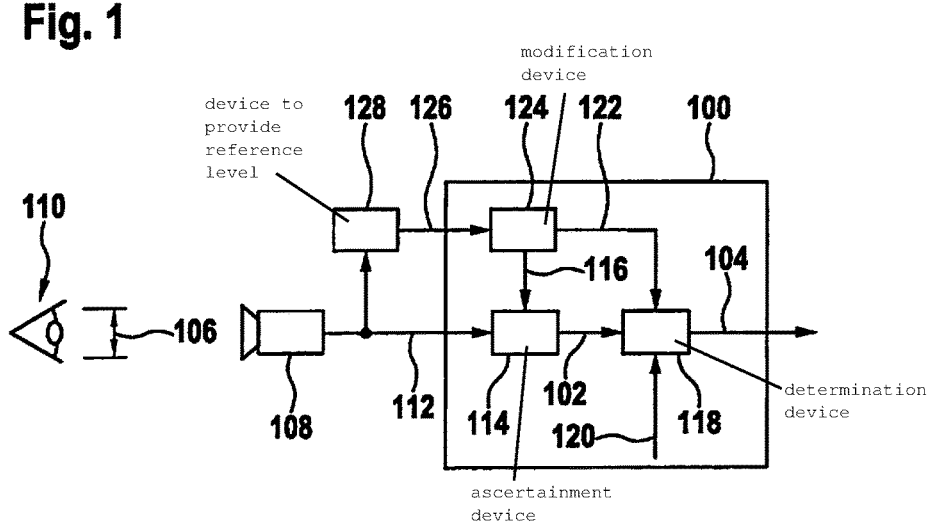
FIG. 1 shows a block circuit diagram of a device for distinguishing blinking events and instrument gazes according to one exemplary embodiment.

In the following description of advantageous exemplary embodiments of the present invention, identical or similar reference numerals are used for elements that have a similar effect and are shown in the various figures. A repeated description of these elements has been omitted.

FIG. 1 shows a block circuit diagram of a device 100 for distinguishing blinking events 102 and instrument gazes 104 according to one exemplary embodiment. In this case, blinking events 102 and instrument gazes 104 are distinguished on the basis of an eye-opening width 106. Eye-opening width 106 is detected by a detection system 108 at one or both eye(s) 110 of a driver of a vehicle and is represented by an opening width value 112. Eye-opening width 106 represents an instantaneous clearance between the eyelids of eye 110. Opening width value 112 is read in by device 100 at an input of device 100. In device 100, opening width value 112 is used in an ascertainment device 114 for ascertaining a blinking event 102 using at least one blinking limit value 116. In the process, the blinking event is determined when opening width value 112 is smaller than blinking limit value 116.

In a determination device 118, an instrument gaze 104 is determined with the aid of a maximum blinking duration 120. In the process, instrument gaze 104 is determined if detected blinking event 102 is detected as lasting longer than maximum blinking duration 120. If opening width value 112 is greater than an open limit value 122 after instrument gaze 104 has been determined, then the next blinking event is determined in determination device 114.

In one exemplary embodiment, device 100 has a modification device 124. Blinking limit value 116 and, alternatively or additionally, open limit value 122 is/are adapted in modification device 124 with the aid of a reference level 126 for eye-opening width 106. Reference level 126 represents eye-opening width 104 when no blinking event 102 and, alternatively or additionally, no instrument gaze 104 is/are occurring. Reference level 126 is provided by a device 128 for providing reference level 126 using opening width value 112.

Based on data from a video camera 108, an instantaneous opening degree 106 of eyes 110 is able to be detected, for which purpose corresponding image processing algorithms are used. In the process, an eye opening level 126 is able to be detected for both eyes 110 in each case.

A common eye opening level 126 may be calculated from eye opening degrees 106 of two eyes 110. The calculation of the instantaneous eye opening level 126 is able to be carried out with the aid of Savitzky-Golay filters.

The approach presented here makes it possible to classify or precisely estimate the drowsiness or a state of drowsiness of a driver with the aid of lid closure data 112, e.g., from a camera 108. It is therefore proposed by way of example to use "fitted" curves to increase the detection quality and to distinguish previously detected blinking.

Figure 2:
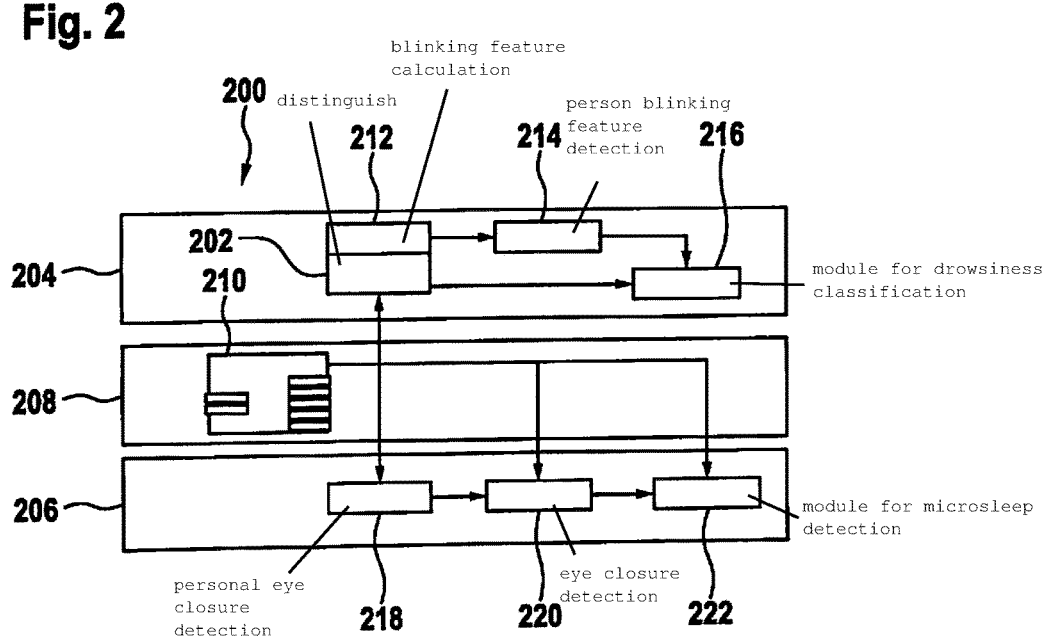
FIG. 2 shows an illustration of an architecture of an overall system for monitoring the drowsiness of a driver of a vehicle according to an exemplary embodiment.

FIG. 2 shows an illustration of an architecture of an overall system 200 for monitoring the drowsiness of a driver of a vehicle according to one exemplary embodiment. The distinguishing 202 of blinking events and instrument gazes proposed here is a component of overall system 200.

Overall system 200 has three main components 204, 206, 208. First main component 204 is referred to as drowsiness classification. Second main component 206 is referred to as microsleep detection, and third main component 208 encompasses modules 210 that are jointly used by drowsiness classification 204 and microsleep detection 206.

Distinguishing 202 introduced here is a component of drowsiness classification 204 and may be referred to as blinking event detection 202.

Modules 210 are able to be described as eye closure preprocessing 210. Eye closure preprocessing 210 includes a detection of the eye closure on the left and right, filtering of the eye closure, an eye closure-rate detection, an acc of the eye closure, a provision of a reference level, and a validation.

Eye closure preprocessing 210 indicates an instantaneous eye closure, an eye closure rate, and the reference level.

In drowsiness classification 204, these values are used in blinking event detection 202, and blinking events are forwarded to a blinking feature calculation 212.

Blinking feature calculation 212 outputs blinking features to a personal blinking feature detection 214 and to a module 216 for drowsiness classification. The module reads in a personal blinking behavior from blinking feature detection 214 and outputs a drowsiness level.

In microsleep detection 206, the values are used in a personal eye closure detection 218, an eye closure detection 220, and in a module 222 for microsleep detection.

Personal eye closure detection 218 outputs a personal open eye level and a personal closed eye level. Both are used by eye closure detection 220 to make a binary eye open value available for module 222. Module 222 outputs microsleep events.

The approach introduced here constitutes an improvement in the detection quality of blinking features on the basis of previously prefiltered eye opening data. The introduced blinking event detection (BED) 202, as it is commonly known, is part of an overall system 200 for detecting drowsiness and/or microsleep events. Overall system 200 includes an eye closure preprocessing 204. An instantaneous eye opening level (EOL) is able to be calculated with the aid of an algorithm. Overall system 200 may include a microsleep detection 206.

Figure 3:
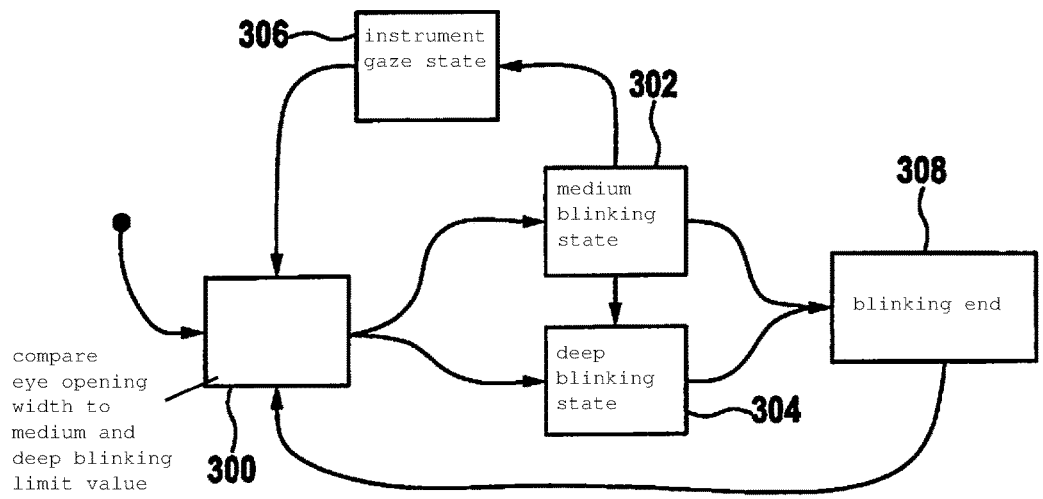
FIG. 3 shows a state diagram for a detection of blinking events according to one exemplary embodiment.

FIG. 3 shows a state diagram for a detection of blinking events according to one exemplary embodiment. Different detection states as a function of an eye-opening width are shown in the state diagram. Starting from an open state 300, the instantaneous eye-opening width is compared to a medium blinking limit value and a deep blinking limit value. If the eye-opening width is smaller than the average blinking limit value, then a medium blinking state 302 is detected. If the eye-opening width is smaller than the deep blinking limit value, a deep blinking state 304 is detected.

If medium blinking state 302 is detected and the eye-opening width becomes smaller than the deep blinking limit value, then deep blinking state 304 is detected.

An instrument gaze state 306 is detected if medium blinking state 302 is detected as lasting longer than a maximum blinking duration.

When the eye-opening width becomes greater than an open limit value following instrument gaze state 306, then open state 300 is detected once again.

When medium blinking state 302 is detected and the eye-opening width becomes greater than the open limit value, a blinking end 308 is detected and a characteristic of the eye-opening width during the blinking event is stored.

In the same way, blinking end 308 is detected when deep blinking state 304 is detected and the eye-opening width becomes greater than the medium blinking limit value. The characteristic of the eye-opening width during the blinking event will then also be stored.

After blinking end 308, the eye has open state 300 once again.

A system is provided for the robust detection of blinking events and for increasing the quality of the sensor signal.

One exemplary embodiment of the algorithm for detecting blinking events and for improving the quality of the input variables introduced here has a step of detecting, a step of fitting, and a step of calculating. This exemplary embodiment is described with the aid of FIGS. 3 and 4.

In the step of detecting, potential blinking events are detected with the aid of predefined limit values of the eye opening.

In this context, blinking events are distinguished from instrument gazes. Instrument gazes have no relation to drowsiness of the driver and may therefore be eliminated in the further course. Potential blinking events are identified with the aid of a state machine and three different limit values. An upper limit value, a medium limit value, and a lower limit value are used in the process. All three utilized limit values (high, medium, and low) are able to be defined as a percentage of the eye opening level (EOL). For example, the upper limit value (high) may always amount to 100% of the eye opening level. The medium limit value (medium) may always amount to 70% of the eye opening level, and the lower limit value (low) may always amount to 20% of the eye opening level. The absolute values are therefore a function of the instantaneous opening of the eye of the driver and are thereby adaptively adjusted to the given situation.

In FIG. 3, the proposed state diagram for detecting blinking events featuring a large and a small amplitude as well as instrument gazes is shown. The display instruments, such as a freely programmable instrument cluster (IC), are referred to as tachometer. Depending on the instantaneous value of an eye-opening signal (EOS), the different states 300, 302, 304, 306, 308 are distinguished.

To differentiate blinking events featuring a small amplitude and instrument gazes, a maximum duration (max_dur) is introduced for the state "medium blink" or a medium blinking event. This maximum duration may be set to 0.5 s, for example.

As soon as the state 308 "save" is reached, the raw data of the blinking event are stored for further processing. To do so, the eye opening data are cut out in a sufficiently large window (e.g., +−2 s around the point featuring the lowest eye-opening degree) and stored. The state machine then immediately returns to state 300 "open".

Figure 4:
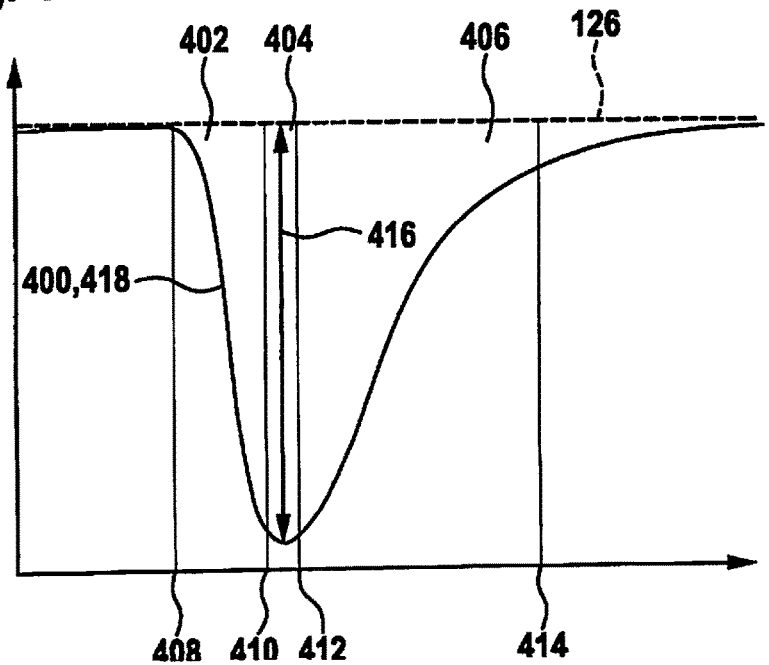
FIG. 4 shows an illustration of an eye opening curve of a blinking event according to one exemplary embodiment.

FIG. 4 shows a representation of an eye opening curve 400 of a blinking event according to one exemplary embodiment. Eye opening curve 400 is shown in a diagram that has a time plotted on its abscissa and a lid opening plotted on its ordinate. Eye opening curve 400 represents an interpolation of a characteristic of individual values of an eye-opening width or a lid opening. As shown in FIG. 3, the characteristic has been retroactively stored in response to a detection of an end of the blinking event.

The blinking event has a closing phase 402, an end phase 404 and an opening phase 406. End phase 404 may also be called a plateau phase 404. Closing phase 402 extends from a blinking start 408 to a plateau start 410. End phase 404 extends from plateau start 410 to a plateau end 412. Opening phase 406 extends from plateau end 412 to a blinking end 414. Within end phase 404, eye opening curve 400 features its local minimum or its maximum negative amplitude 416 during the blinking event.

Prior to blinking start 408 and following blinking end 414, eye opening curve 400 reaches an instantaneous reference level 126 of the eye-opening width as a maximum value, which is a function of an instantaneous light situation, for instance.

In the event that the sensor used is still insufficiently accurate or has an insufficient frame rate, then the detected potential blinking events are able to be refined in a further step, as described in FIG. 3. To do so, fitting with a predefined curve 418 is carried out for all windows detected in the first step. This curve 418 reproduces the ideal characteristic of a blinking event.

In the step of fitting, these blinking events are fitted with predefined curves 418 in order to compensate for a low image repeat frequency of the used image sensor, which has an effect similar to an increase in the frame rate of the sensor.

FIG. 4 shows an idealized characteristic 400 of a blinking event. In this case, curve 418 has the shape of a horizontal straight line prior to blinking start 408, for example. In closing phase 402, curve 418 has the shape of a descending curve, e.g., of the fifth order. In plateau phase 404, curve 418 has the shape of a horizontal straight line, and in opening phase 406, curve 418 has the shape of an ascending curve, e.g., of the fifth order. Following blinking end 414, curve 418 has the shape of a horizontal straight line, for example.

Under the marginal condition, curve 418 is adapted to the characteristic of individual values such that resulting overall curve 400 as well as its first derivation have a steady characteristic in the entire examined window.

In this case, the starting point and the end point of curve 400 result from the boundaries of the window detected in the preceding step. The other instants in time 408, 410, 412, 414 result in an optimization phase of the fitting. In other words, different coefficients of curve components 402, 404, 406 result for the individual time ranges. On the one hand, they may be subjected to further analytical processing, but it is also possible to calculate any finely graduated interpolation of curve 418. The method shown here is thus able to increase the sample rate of the sensor signal by way of the interpolation.

In one exemplary embodiment, the fitting is optimized in such a way that an error function becomes minimal. Suitable in this context, for example, is the sum of the square deviation of the measured values with fitted curve 418, which should be minimal.

In the step of calculating, a quality measure for the quality of the fitting is calculated.

In a further, optional step, the error function calculated in the previous step may be used in a further optional step to exclude from the further processing blinking events that have an implausible characteristic 400, i.e., blinking events that do not correspond to the ideal characteristic. To do so, the result of the error function may be compared to a previously defined limit value. If this limit value is exceeded for a specific blinking event, then it is no longer utilized in the subsequent calculations for the classification of the drowsiness.

Figure 5:
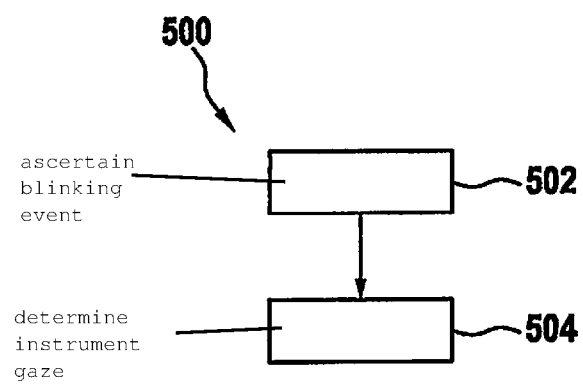
FIG. 5 shows a flow diagram of a method for distinguishing blinking events and instrument gazes according to one exemplary embodiment.

FIG. 5 shows a flow diagram of a method 500 for distinguishing blinking events and instrument gazes according to one exemplary embodiment. For example, the method may be executed on a device as illustrated in FIG. 1. Method 500 has a step 502 of ascertaining and a step 504 of determining.

In step 502 of ascertaining, a blinking event is ascertained using at least one blinking limit value. The blinking event is ascertained when an opening width value which represents a value of an eye-opening width is smaller than the blinking limit value. The eye-opening width represents an instantaneously detected clearance between the eyelids of an eye.

In step 504 of determining, an instrument gaze is determined on the basis of a maximum blinking duration. The instrument gaze is determined when the detected blinking event is detected as lasting longer than the maximum blinking duration.

In one exemplary embodiment, steps 502, 504 of the present method are carried out anew if the opening width value is greater than an open limit value following determination 504 of the instrument gaze.

If an exemplary embodiment includes an "and/or" linkage between a first feature and a second feature, then this is meant to indicate that the exemplary embodiment according to one specific embodiment includes both the first feature and the second feature, and according to a further specific embodiment, includes either only the first feature or only the second feature.

What is claimed is:

1. A method for distinguishing blinking events and instrument gazes using an eye-opening width, the eye-opening width representing an instantaneously detected clearance between eyelids of an eye, the method comprising:
receiving, by a control unit including hardware, video data from a video camera, the video data including images of eyes of a driver;
determining, using the control unit, an opening width value based on the received video data, the opening width value representing a value of the eye-opening width;
ascertaining, using the control unit, the opening width value is smaller than a blinking limit value;
ascertaining, using the control unit, a blinking event based on ascertaining the opening width value is smaller than the blinking limit value;
determining, using the control unit, based on the received video data, a duration of the ascertained blinking event and determining the duration of the ascertained blinking event lasted longer than the maximum blinking duration;
determining, using the control unit, an instrument gaze based on determining the duration of the ascertained blinking event lasted longer than the maximum blinking duration; and
outputting, by the determination device, a control signal or a data signal indicating the determined instrument gaze;
wherein the steps of the method are carried out anew when the opening width value is greater than an open limit value following the determination of the instrument gaze.

2. The method as recited in claim 1, wherein, in the ascertaining step, a medium blinking event is ascertained when the opening width value is smaller than a medium blinking limit value, a deep blinking event is ascertained when the opening width value is smaller than a deep blinking limit value, and a deep blinking event is ascertained when an opening width value is smaller than the deep blinking limit value following the ascertaining of the medium blinking event.

3. The method as recited in claim 2, wherein the instrument gaze is determined in the determining step when the medium blinking event is ascertained as lasting longer than the maximum blinking duration.

4. The method as recited in claim 1, further comprising:
storing a time characteristic of the opening width value as a blinking event characteristic when the opening width value is greater than the blinking limit value following the ascertaining of the blinking event, the steps of the method being executed anew following the step of storing.

5. The method as recited in claim 4, further comprising:
interpolating the opening width values of the blinking event characteristic to connect them into a curve.

6. The method as recited in claim 5, wherein in the step of interpolating, the curve is approximated using a predefined curve shape.

7. The method as recited in claim 6, wherein in the step of interpolating, at least one deviation value of at least one of the opening width values from the curve is determined.

8. The method as recited in claim 7, further comprising:
plausibilizing, wherein in the plausibilizing, the blinking event characteristic is discarded when the at least one deviation value or a value derived therefrom is greater than a deviation limit value.

9. The method as recited in claim 1, further comprising:
modifying, in which at least one of the blinking limit value and the open limit value is adapted using a reference level for the eye-opening width, the reference level representing the eye-opening width when at least one of no blinking event and an instrument gaze is occurring.

10. The method as recited in claim 2, wherein the medium blinking limit value is a value representing 70% of a reference eye opening level, and the deep blinking value is a value representing 20% of the reference eye opening level.

11. A device for distinguishing blinking events and instrument gazes using an eye-opening width, the eye-opening width representing an instantaneously detected clearance between eyelids of an eye, the device configured to:
receive video data from a video camera, the video data including images of eyes of a driver;
ascertain, based on the received video data, a blinking event using at least one blinking limit value, the blinking event being ascertained when an opening width value representing a value of the eye-opening width is smaller than the blinking limit value;
determine, based on the received video data, a duration of the ascertained blinking event;
determine an instrument gaze using a maximum blinking duration, the instrument gaze being determined when the determined duration of the ascertained blinking event is detected as lasting longer than the maximum blinking duration; and
output a control signal or a data signal indicating the determined instrument gaze;
wherein the device is configured to carry out the receiving, the ascertaining, the determining of the duration, and the determining of the instrument gaze anew when the opening width value is greater than an open limit value following the determination of the instrument gaze;
wherein the device is a control unit including hardware.

12. The device as recited in claim 11, wherein, in the ascertainment of the blinking event, a medium blinking event is ascertained when the opening width value is smaller than a medium blinking limit value, a deep blinking event is ascertained when the opening width value is smaller than a deep blinking limit value, and the deep blinking event is ascertained when an opening width value is smaller than the deep blinking limit value following the ascertaining of the medium blinking event.

13. The device as recited in claim 12, wherein the medium blinking limit value is a value representing 70% of a reference eye opening level, and the deep blinking value is a value representing 20% of the reference eye opening level.

14. The device as recited in claim 12, wherein the instrument gaze is determined when the medium blinking event is ascertained as lasting longer than the maximum blinking duration.

15. The device as recited in claim 14, wherein no instrument gaze is determined when the deep blinking event is ascertained as lasting longer than the maximum blinking duration.

16. A non-transitory machine-readable storage medium on which is stored a computer program for distinguishing blinking events and instrument gazes using an eye-opening width, the eye-opening width representing an instantaneously detected clearance between eyelids of an eye, the computer program, when executed by a processor, causing the processor to perform:
receiving, by a control unit including hardware, video data from a video camera, the video data including images of eyes of a driver;
determining, using the control unit, an opening width value based on the received video data, the opening width value representing a value of the eye-opening width;
ascertaining, using the control unit, the opening width value is smaller than a blinking limit value;
ascertaining, using the control unit, a blinking event based on ascertaining the opening width value is smaller than the blinking limit value;
determining, using the control unit, based on the received video data, a duration of the ascertained blinking event and determining the duration of the ascertained blinking event lasted longer than the maximum blinking duration;
determining, using the control unit, an instrument gaze, distinct from a deep blinking event, based on determining the duration of the ascertained blinking event lasted longer than the maximum blinking duration; and
outputting, by the determination device, a control signal or a data signal indicating the determined instrument gaze, distinct from the deep blinking event;
wherein the steps of the method are carried out anew when the opening width value is greater than an open limit value following the determination of the instrument gaze.

17. A device for distinguishing blinking events and instrument gazes using an eye-opening width, the eye-opening width representing an instantaneously detected clearance between eyelids of an eye, the device configured to:
receive video data from a video camera, the video data including images of eyes of a driver;
ascertain, based on the received video data, a possible blinking event using at least one blinking limit value, the possible blinking event being ascertained when an opening width value representing a value of the eye-opening width is smaller than the blinking limit value;
determine, based on the received video data, a duration of the ascertained blinking event;
determine an instrument gaze using a maximum blinking duration, the instrument gaze being determined when the determined duration of the ascertained possible blinking event is detected as lasting longer than the maximum blinking duration;
determine a blinking event when the determined duration of the ascertained possible blinking event is does not last longer than the maximum blinking duration;
output, when the instrument gaze is determined, a control signal or a data signal indicating the determined instrument gaze, distinct from the blinking event;
output, when the blinking event is determined, a signal indicating the determined blinking event, distinct from the instrument gaze, the signal indicating the determining blinking event being used for drowsiness classification;

wherein the device is configured to carry out the receiving, the ascertaining, the determining of the duration, and the determining of the instrument gaze anew when the opening width value is greater than an open limit value following the determination of the instrument gaze;

wherein the device is a control unit including hardware.

* * * * *